US010881317B2

(12) United States Patent
Perschbacher et al.

(10) Patent No.: US 10,881,317 B2
(45) Date of Patent: Jan. 5, 2021

(54) POST-HOC ATRIAL FIBRILLATION DETECTION

(71) Applicant: Cardiac Pacemakers, Inc., St. Paul, MN (US)

(72) Inventors: David L. Perschbacher, Coon Rapids, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 275 days.

(21) Appl. No.: 15/901,336

(22) Filed: Feb. 21, 2018

(65) Prior Publication Data

US 2018/0256053 A1   Sep. 13, 2018

Related U.S. Application Data

(60) Provisional application No. 62/468,194, filed on Mar. 7, 2017.

(51) Int. Cl.
*A61B 5/04* (2006.01)
*A61B 5/046* (2006.01)
(Continued)

(52) U.S. Cl.
CPC .......... *A61B 5/046* (2013.01); *A61B 5/04012* (2013.01); *A61B 5/4836* (2013.01);
(Continued)

(58) Field of Classification Search
CPC ..... A61B 5/046; A61B 5/04012; A61B 5/686; A61B 5/4836; A61N 1/3962;
(Continued)

(56) References Cited

U.S. PATENT DOCUMENTS 5,562,709 A   10/1996   White
5,622,178 A   4/1997   Gilham
(Continued)

FOREIGN PATENT DOCUMENTS

AU   2015301633 B2   8/2018
CN       1829554 A    9/2006
(Continued)

OTHER PUBLICATIONS

"U.S. Appl. No. 14/825,669, Response filed Apr. 24, 2017 to Final Office Action dated Mar. 9, 2017", 12 pgs.
(Continued)

*Primary Examiner* — Rex R Holmes
(74) *Attorney, Agent, or Firm* — Schwegman Lundberg & Woessner. P.A.

(57) ABSTRACT

An apparatus comprises an arrhythmia detection circuit configured to: detect atrial arrhythmia in a first portion of a sensed cardiac signal using a first arrhythmia detection criteria, wherein the sensed cardiac signal is representative of cardiac activity of a subject; and upon detection of the atrial arrhythmia, analyze a second portion of the cardiac signal that is prior in time to the first portion using a second different arrhythmia detection criteria to detect the presence or absence of the atrial arrhythmia in the second portion of the cardiac signal.

19 Claims, 8 Drawing Sheets

(51) Int. Cl.
*A61N 1/39* (2006.01)
*A61N 1/365* (2006.01)
*A61B 5/00* (2006.01)
*A61N 1/02* (2006.01)
*A61N 1/362* (2006.01)

(52) U.S. Cl.
CPC .............. *A61B 5/686* (2013.01); *A61N 1/025* (2013.01); *A61N 1/365* (2013.01); *A61N 1/3621* (2013.01); *A61N 1/36507* (2013.01); *A61N 1/395* (2013.01); *A61N 1/3956* (2013.01); *A61N 1/3962* (2013.01); *A61N 1/3987* (2013.01)

(58) Field of Classification Search
CPC ...... A61N 1/3621; A61N 1/365; A61N 1/395; A61N 1/3987; A61N 1/36507; A61N 1/3956; A61N 1/025
See application file for complete search history.

(56) References Cited

U.S. PATENT DOCUMENTS

| | | |
|---|---|---|
| 6,490,479 B2 | 12/2002 | Bock |
| 6,931,273 B2 | 8/2005 | Groenewegen et al. |
| 7,031,765 B2 | 4/2006 | Ritscher et al. |
| 7,115,096 B2 | 10/2006 | Siejko et al. |
| 7,308,306 B1 | 12/2007 | Park et al. |
| 7,353,057 B2 | 4/2008 | Schiessle et al. |
| 7,412,282 B2 | 8/2008 | Houben |
| 7,566,308 B2 | 7/2009 | Stahmann |
| 7,596,405 B2 | 9/2009 | Kurzweil et al. |
| 7,634,310 B2 | 12/2009 | Lee et al. |
| 7,657,307 B2 | 2/2010 | Van Dam et al. |
| 7,899,531 B1 | 3/2011 | Benser et al. |
| 7,904,142 B2 | 3/2011 | Kim et al. |
| 7,970,468 B1 | 6/2011 | Ostrow |
| 8,195,280 B2 | 6/2012 | Van Dam et al. |
| 8,326,407 B2 | 12/2012 | Linker |
| 8,560,058 B2 | 10/2013 | Babaeizadeh et al. |
| 8,639,316 B2 | 1/2014 | Sarkar |
| 9,999,368 B2 | 6/2018 | Perschbacher et al. |
| 10,542,902 B2 | 1/2020 | Perschbacher et al. |
| 10,617,320 B2 | 4/2020 | Mahajan et al. |
| 2001/0034539 A1 | 10/2001 | Stadler et al. |
| 2002/0065473 A1 | 5/2002 | Wang et al. |
| 2004/0092836 A1 | 5/2004 | Ritscher et al. |
| 2005/0080347 A1 | 4/2005 | Sheth et al. |
| 2005/0154421 A1* | 7/2005 | Ousdigian ............ A61B 5/0464 607/14 |
| 2006/0195037 A1 | 8/2006 | Wiesel |
| 2006/0247548 A1 | 11/2006 | Sarkar et al. |
| 2007/0038253 A1 | 2/2007 | Kim et al. |
| 2007/0100248 A1 | 5/2007 | Van Dam et al. |
| 2008/0161703 A1 | 7/2008 | Houben et al. |
| 2008/0188764 A1 | 8/2008 | Lee et al. |
| 2008/0288009 A1 | 11/2008 | Kim et al. |
| 2009/0112110 A1 | 4/2009 | Zhang |
| 2010/0057152 A1 | 3/2010 | Kim et al. |
| 2010/0168597 A1 | 7/2010 | Kim et al. |
| 2010/0274149 A1 | 10/2010 | Li et al. |
| 2010/0305642 A1 | 12/2010 | Dong et al. |
| 2011/0152957 A1 | 6/2011 | Shaquer |
| 2012/0004566 A1 | 1/2012 | Zhang et al. |
| 2012/0035489 A1 | 2/2012 | Dong et al. |
| 2012/0101541 A1 | 4/2012 | Corbucci et al. |
| 2012/0238891 A1 | 9/2012 | Sarkar et al. |
| 2012/0238892 A1 | 9/2012 | Sarkar |
| 2013/0150911 A1 | 6/2013 | Perschbacher et al. |
| 2013/0296680 A1 | 11/2013 | Linker |
| 2014/0323894 A1 | 10/2014 | Zhang et al. |
| 2015/0088216 A1 | 3/2015 | Gordon et al. |
| 2016/0045125 A1 | 2/2016 | Krueger et al. |
| 2016/0175603 A1 | 6/2016 | Sheldon et al. |
| 2016/0287115 A1 | 10/2016 | Perschbacher et al. |
| 2017/0027462 A1 | 2/2017 | Mahajan et al. |
| 2017/0127965 A1* | 5/2017 | Krueger ............... A61N 1/3956 |
| 2018/0242869 A1 | 8/2018 | Perschbacher et al. |

FOREIGN PATENT DOCUMENTS

| | | |
|---|---|---|
| CN | 1989897 A | 7/2007 |
| CN | 101925381 A | 12/2010 |
| CN | 101969842 A | 2/2011 |
| CN | 106659407 A | 5/2017 |
| CN | 107529988 A | 1/2018 |
| CN | 107847746 A | 3/2018 |
| CN | 110573211 A | 12/2019 |
| CN | 106659407 B | 4/2020 |
| EP | 2407097 A1 | 1/2012 |
| EP | 3259027 A1 | 12/2017 |
| EP | 3277372 A1 | 2/2018 |
| EP | 3277372 B1 | 8/2019 |
| JP | H10127590 A | 5/1998 |
| JP | H10504897 A | 5/1998 |
| JP | H11503038 A | 3/1999 |
| JP | 2004524074 A | 8/2004 |
| JP | 2006524106 A | 10/2006 |
| JP | 2008539015 A | 11/2008 |
| JP | 2009089883 A | 4/2009 |
| JP | 2012527958 A | 11/2012 |
| JP | 2013535236 A | 9/2013 |
| JP | 2017527356 A | 9/2017 |
| JP | 2018511400 A | 4/2018 |
| JP | 2018523518 A | 8/2018 |
| JP | 6434129 B2 | 11/2018 |
| JP | 6525461 B2 | 5/2019 |
| JP | 6653372 B2 | 1/2020 |
| JP | 2019548737 A | 4/2020 |
| WO | WO-2006118852 A2 | 11/2006 |
| WO | WO-2013020710 A1 | 2/2013 |
| WO | WO-2016025704 A1 | 2/2016 |
| WO | WO-2016134161 A1 | 8/2016 |
| WO | WO-2016160674 A1 | 10/2016 |
| WO | WO-2017019178 A1 | 2/2017 |
| WO | WO-2017079245 A1 | 5/2017 |
| WO | WO-2018164840 A1 | 9/2018 |

OTHER PUBLICATIONS

"U.S. Appl. No. 14/825,669, Advisory Action dated May 3, 2017", 3 pgs.

"U.S. Appl. No. 14/825,669, Appeal Brief filed Dec. 26, 2017", 17 pgs.

"U.S. Appl. No. 14/825,669, Final Office Action dated Mar. 9, 2017", 13 pgs.

"U.S. Appl. No. 14/825,669, Non Final Office Action dated Jun. 23, 2017", 9 pgs.

"U.S. Appl. No. 14/825,669, Non Final Office Action dated Sep. 27, 2016", 9 pgs.

"U.S. Appl. No. 14/825,669, Response filed Jun. 8, 2017 to Final Office Action dated Mar. 9, 2017", 14 pgs.

"U.S. Appl. No. 15/082,440, Corrected Notice of Allowance dated Feb. 9, 2018", 5 pgs.

"U.S. Appl. No. 15/082,440, Examiner Interview Summary dated Sep. 6, 2017", 2 pgs.

"U.S. Appl. No. 15/082,440, Non Final Office Action dated Jun. 21, 2017", 9 pgs.

"U.S. Appl. No. 15/082,440, Notice of Allowance dated Jan. 18, 2018", 8 pgs.

"U.S. Appl. No. 15/082,440, Notice of Allowance dated Sep. 25, 2017", 10 pgs.

"U.S. Appl. No. 15/082,440, Response filed May 17, 2017 to Restriction Requirement dated May 30, 2017", 9 pgs.

"U.S. Appl. No. 15/082,440, Response filed Sep. 5, 2017 to Non Final Office Action dated Jun. 21, 2017", 14 pgs.

"U.S. Appl. No. 15/082,440, Restriction Requirement dated Mar. 30, 2017", 7 pgs.

"U.S. Appl. No. 15/175,151, Response filed Jan. 23, 2018 to Restriction Requirement dated Dec. 7, 2017", 9 pgs.

(56) References Cited

OTHER PUBLICATIONS

"U.S. Appl. No. 15/175,151, Restriction Requirement dated Dec. 7, 2017", 6 pgs.
"Application Serial No. PCT/US2016/036146, Invitation to Pay Add'l Fees and Partial Search Report dated Oct. 6, 2016", 7 pgs.
"Australian Application Serial No. 2015301633, First Examiners Report dated Sep. 7, 2017", 3 pgs.
"European Application Serial No. 15757059.9, Response filed Sep. 26, 2017 to Communication Pursuant to Rules 161(1) and 162 EPC dated Mar. 21, 2017", 18 pgs.
"International Application Serial No. PCT/US2015/045042, International Preliminary Report on Patentability dated Feb. 23, 2017", 10 pgs.
"International Application Serial No. PCT/US2015/045042, International Search Report dated Oct. 27, 2015", 6 pgs.
"International Application Serial No. PCT/US2015/045042, Written Opinion dated Oct. 27, 2015", 9 pgs.
"International Application Serial No. PCT/US2016/024463, International Preliminary Report on Patentability dated Oct. 12, 2017", 8 pgs.
"International Application Serial No. PCT/US2016/024463, International Search Report dated Jun. 17, 2016", 6 pgs.
"International Application Serial No. PCT/US2016/024463, Written Opinion dated Jun. 17, 2016", 6 pgs.
"International Application Serial No. PCT/US2016/036146, International Preliminary Report on Patentability dated Feb. 8, 2018", 12 pgs.
"International Application Serial No. PCT/US2016/036146, International Search Report dated Dec. 7, 2016", 5 pgs.
"International Application Serial No. PCT/US2016/036146, Written Opinion dated Dec. 7, 2016", 10 pgs.
"International Application Serial No. PCT/US2016/060050, International Search Report dated Feb. 6, 2017", 4 pgs.
"International Application Serial No. PCT/US2016/060050, Written Opinion dated Feb. 6, 2017", 5 pgs.
Babaeizadeh, Saeed, et al., "Improvements in atrial fibrillation detection for real-time monitoring", Journal of Electrocardiology, Elsevier Science vol. 42, No. 6,, (Nov. 1, 2009), 522-526.
Esperer, et al., "Cardiac arrhythmias imprint specific signatures on Lorenz plots", Ann Noninvasive Electrocardiol, (2008), 44-60 pgs.
Pürerfellner, H., et al., "P-wave evidence as a method for improving algorithm to detect atrial fibrillation in insertable cardiac monitors", Heart Rhythm; vol. 11, Issue 9, (Sep. 2014), 1575-1583.
Tateno, K, et al., "Automatic detection of atrial fibrillation using the coefficient of variation and density histograms of RR and RR intervals", Medical and Biological Engineering and Computing, vol. 39, No. 6 (Nov. 1, 2011), 664-671.
"U.S. Appl. No. 15/175,151, Advisory Action dated Sep. 12, 2019", 3 pgs.
"U.S. Appl. No. 15/175,151, Advisory Action dated Oct. 2, 2018", 3 pgs.
"U.S. Appl. No. 15/175,151, Advisory Action dated Oct. 23, 2019", 4 pgs.
"U.S. Appl. No. 15/175,151, Examiner Interview Summary dated Jan. 21, 2020", 3 pgs.
"U.S. Appl. No. 15/175,151, Final Office Action dated Jul. 5, 2019", 8 pgs.
"U.S. Appl. No. 15/175,151, Final Office Action dated Aug. 2, 2018", 10 pgs.
"U.S. Appl. No. 15/175,151, Non Final Office Action dated Feb. 23, 2018", 10 pgs.
"U.S. Appl. No. 15/175,151, Non Final Office Action dated Dec. 31, 2018", 8 pgs.
"U.S. Appl. No. 15/175,151, Notice of Allowance dated Dec. 4, 2019", 7 pgs.
"U.S. Appl. No. 15/175,151, Response filed May 14, 2018 to Non Final Office Action dated Feb. 23, 2018", 14 pgs.
"U.S. Appl. No. 15/175,151, Response filed Sep. 3, 2019 to Final Office Action dated Jul. 5, 2019", 12 pgs.
"U.S. Appl. No. 15/175,151, Response filed Sep. 25, 2018 to Final Office Action dated Aug. 2, 2018", 11 pgs.
"U.S. Appl. No. 15/175,151, Response filed Oct. 7, 2019 to Advisory Action dated Sep. 12, 2019", 13 pgs.
"U.S. Appl. No. 15/175,151, Response filed Mar. 25, 2019 to Non Final Office Action dated Dec. 31, 2018", 11 pgs.
"U.S. Appl. No. 15/175,151,Pre-Appeal Brief Request for Review filed Nov. 4, 2019", 5 pgs.
"U.S. Appl. No. 15/967,326, Advisory Action dated Mar. 14, 2019", 3 pgs.
"U.S. Appl. No. 15/967,326, Final Office Action dated Jan. 3, 2019", 11 pgs.
"U.S. Appl. No. 15/967,326, Final Office Action dated Aug. 7, 2019", 6 pgs.
"U.S. Appl. No. 15/967,326, Non Final Office Action dated Apr. 18, 2019", 9 pgs.
"U.S. Appl. No. 15/967,326, Non Final Office Action dated Jun. 29, 2018", 9 pgs.
"U.S. Appl. No. 15/967,326, Notice of Allowance dated Sep. 16, 2019", 7 pgs.
"U.S. Appl. No. 15/967,326, Response filed Feb. 21, 2019 to Final Office Action dated Jan. 3, 2019", 11 pgs.
"U.S. Appl. No. 15/967,326, Response filed Jul. 18, 2019 to Non Final Office Action dated Apr. 18, 2019", 8 pgs.
"U.S. Appl. No. 15/967,326, Response filed Aug. 20, 2019 to Final Office Action dated Aug. 7, 2019", 8 pgs.
"U.S. Appl. No. 15/967,326, Response filed Sep. 24, 2018 to Non Final Office Action dated Jun. 29, 2018", 13 pgs.
"Australian Application Serial No. 2015301633, Response filed Mar. 21, 2018 to First Examiners Report dated Sep. 7, 2017", 14 pgs.
"Chinese Application Serial No. 201580047246.7, Office Action dated Mar. 6, 2019", w/ English Translation, 19 pgs.
"Chinese Application Serial No. 201580047246.7, Office Action dated Sep. 19, 2019", W/ English Translation, 10 pgs.
"Chinese Application Serial No. 201580047246.7, Response Filed Jul. 22, 2019 to Office Action dated Mar. 6, 2019", w/English Claims, 17 pgs.
"Chinese Application Serial No. 201580047246.7, Response filed Dec. 4, 2019 to Office Action dated Sep. 19, 2019", w/ English claims, 13 pgs.
"Chinese Application Serial No. 201580047246.7, Response to Examiner Telephone Interview filed Dec. 18, 2019", w/ English claims, 10 pgs.
"European Application Serial No. 16715709.8, Response filed Jun. 27, 2018 to Communication Pursuant to Rules 161(1) and 162 EPC dated Dec. 7, 2017", 28 pgs.
"European Application Serial No. 16730174.6, Communication Pursuant to Article 94(3) EPC dated Dec. 18, 2018", 6 pgs.
"European Application Serial No. 16730174.6, Communication Pursuant to Article 94(3) EPC dated May 28, 2019", 5 pgs.
"European Application Serial No. 16730174.6, Response filed Apr. 18, 2019 to Communication Pursuant to Article 94(3) EPC dated Dec. 18, 2018", 19 pgs.
"European Application Serial No. 16730174.6, Response filed Sep. 25, 2018 to Communication Pursuant to Rules 161 and 162 EPC dated Mar. 23, 2018", 29 pgs.
"European Application Serial No. 16730174.6, Response filed Sep. 30, 2019 to Communication Pursuant to Article 94(3) EPC dated May 28, 2019", 14 pgs.
"International Application Serial No. PCT/US2018/018974, International Preliminary Report on Patentability dated Sep. 19, 2019", 8 pgs.
"International Application Serial No. PCT/US2018/018974, International Search Report dated Apr. 20, 2018", 5 pgs.
"International Application Serial No. PCT/US2018/018974, Written Opinion dated Apr. 20, 2018", 6 pgs.
"Japanese Application Serial No. 2017-508064, Office Action dated Mar. 6, 2018", With English Translation, 4 pgs.
"Japanese Application Serial No. 2017-508064, Response filed May 30, 2018 to Office Action dated Mar. 6, 2018", w/ English claims, 10 pgs.

(56) References Cited

OTHER PUBLICATIONS

"Japanese Application Serial No. 2017-550731, Notification of Reasons for Refusal dated Dec. 18, 2018", w/ English summary, 6 pgs.

"Japanese Application Serial No. 2017-550731, Office Action dated Sep. 4, 2018", w/ English translation (machine), 8 pgs.

"Japanese Application Serial No. 2017-550731, Response filed Mar. 15, 2019 to Notification of Reasons for Refusal dated Dec. 18, 2018", w/ English claims, 6 pgs.

"Japanese Application Serial No. 2017-550731, Response filed Nov. 28, 2018 to Office Action dated Sep. 4, 2018", w/ English claims, 8 pgs.

"Japanese Application Serial No. 2018-504913, Notification of Reasons for Rejection dated Nov. 13, 2018", W/English Translation, 12 pgs.

"Japanese Application Serial No. 2018-504913, Response filed Apr. 15, 2019 to Notification of Reasons for Rejection dated Nov. 13, 2018", w/ English claims, 11 pgs.

"Japanese Application Serial No. 2018-504913, Response filed Dec. 2, 2019 to Final Notification of Reasons for Refusal dated Sep. 3, 2019", w/ English claims, 8 pgs.

"U.S. Appl. No. 14/825,669, Appeal Decision mailed May 13, 2020", 13 pgs.

"Chinese Application Serial No. 201680018682.6, Office Action dated May 26, 2020", With English Translation, 8 pgs.

"Chinese Application Serial No. 201680018682.6, Response filed Apr. 10, 2020 to Office Action dated Dec. 2, 2019", w/ English Claims, 14 pgs.

"Chinese Application Serial No. 201680044683.8, Office Action dated Jun. 17, 2020", 10 pgs.

"European Application Serial No. 15757059.9, Communication Pursuant to Article 94(3) EPC dated Jul. 2, 2020", 5 pgs.

"European Application Serial No. 18708317.5, Response to Communication Pursuant to Rules 161(1) and 162 EPC filed Mar. 20, 2020", 24 pgs.

U.S. Appl. No. 14/825,669, filed Aug. 13, 2015, Atrial Fibrillation Detection Using Ventricular Rate Variability.

U.S. Appl. No. 15/082,440, filed Mar. 28, 2016, Atrial Fibrillation Detection.

U.S. Appl. No. 15/175,151, filed Jun. 7, 2016, A Method to Trigger an Atrial Fibrillation Electrogram in an Implantable Device That Detects R-Waves.

* cited by examiner

POST-HOC ATRIAL FIBRILLATION DETECTION

CLAIM OF PRIORITY

This application claims the benefit of priority under 35 U.S.C. § 119(e) of U.S. Provisional Patent Application Ser. No. 62/468,194, filed on Mar. 7, 2017, which is herein incorporated by reference in its entirety.

BACKGROUND

Ambulatory medical devices include implantable medical devices (IMDs), wearable medical devices, handheld medical devices, and other medical devices. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition.

Some implantable medical devices can be diagnostic-only devices, such as implantable loop recorders (ILRs), implantable cardiac monitors, and subcutaneously implantable heart failure monitors (SubQ HFMs). The devices may include electrodes in communication with one or more sense amplifiers to monitor electrical heart activity within a patient, or can include one or more sensors to monitor one or more other patient parameters. Subcutaneously implantable devices may include electrodes that are able to sense cardiac signals without being in direct contact with the patient's heart. Other examples of IMDs include implantable drug delivery systems or implantable devices with neural stimulation capability (e.g., vagus nerve stimulator, baroreflex stimulator, carotid sinus stimulator, spinal cord stimulator, deep brain stimulator, etc.).

Some examples of wearable medical devices include wearable cardioverter defibrillators (WCDs) and wearable diagnostic devices (e.g., an ambulatory monitoring vest, holter monitor, cardiac event monitor, or mobile cardiac telemetry devices). WCDs can be monitoring devices that include surface electrodes. The surface electrodes may be arranged to provide one or both of monitoring to provide surface electrocardiograms (ECGs) and delivery of cardioverter and defibrillator shock therapy. In some examples, a wearable medical device can also include a monitoring patch worn by the patient such as an adherable patch or can be included with an article of clothing worn by the patient.

Some examples of handheld medical devices include smartphones and personal data assistants (PDAs). The handheld devices can be diagnostic devices that record an electrocardiograph (ECG) or other physiological parameter while the device is resting in the patient's hand or being held to the patient's chest.

CFM devices can be implantable but in some situations may not include dedicated atrial sensing capability. Additionally, some diagnostic-only implantable, wearable, and handheld devices do not include dedicated atrial sensing capability. Patients with these types of devices may develop atrial arrhythmias, such as atrial fibrillation (AF) for example. This may be especially true for heart failure patients who typically have a high incidence of AF. Knowledge that a specific patient is experiencing AF and the amount time the patient spend in AF can be useful to physicians and clinicians for diagnostic purposes or to tailor a treatment for the patient.

OVERVIEW

It can be desirable for ambulatory medical devices to correctly detect and identify cardiac arrhythmias. This can help to provide the most effective device-based therapy or non-device based therapy (e.g., drug therapy) for the patient. The present subject matter relates to improving the detection or classification of atrial fibrillation and recording the fibrillation episode.

Example 1 can include subject matter (such as an apparatus) comprising an arrhythmia detection circuit. The arrhythmia detection circuit is configured to: detect an episode of cardiac arrhythmia in the sensed cardiac signal using one or more first arrhythmia detection criteria and begin timing the duration of the arrhythmia episode; apply different arrhythmia detection criteria to a duration of the sensed cardiac signal prior to the detected episode of arrhythmia when the episode of arrhythmia is detected.

In Example 2, the subject matter of Example 1 optionally includes a sensing circuit configured to generate a sensed cardiac signal representative of cardiac activity of a subject and operatively coupled to the arrhythmia detection circuit. The arrhythmia detection circuit is configured to add the duration of the prior sensed cardiac signal to the time duration of the arrhythmia episode when arrhythmia is detected in the prior sensed cardiac signal using the different AF detection criteria; and generate a value of total time duration of the detected arrhythmia episode.

In Example 3, the subject matter of one or both of Examples 1 and 2 optionally includes an arrhythmia detection circuit configured to: detect an episode of atrial fibrillation (AF) in the sensed cardiac signal using one or more first AF detection criteria and begin timing the duration of the AF episode; apply different AF detection criteria to a duration of the sensed cardiac signal prior to the detected episode of AF when the episode of AF is detected; add the duration of the prior sensed cardiac signal to the time duration of the AF episode when AF is detected in the prior sensed cardiac signal using the different AF detection criteria; and generate a value of total time duration of the detected AF episode.

In Example 4, the subject matter of one or any combination of Examples 1-3 optionally includes an arrhythmia detection circuit is configured to detect the episode of AF from the sensed cardiac signal using a plurality of AF detection criteria having first specificity and first sensitivity to AF detection, and apply a subset of the first AF detection criteria to a segment of the cardiac signal sensed prior to the detected episode of AF with at least one of different specificity or different sensitivity than the first AF detection criterion.

In Example 5, the subject matter of one or any combination of Examples 1-4 optionally includes an arrhythmia detection circuit configured to detect the episode of AF when sensed ventricular depolarization intervals (V-V intervals) satisfy one or more of a specified V-V interval dispersion threshold, a specified V-V interval double decrement threshold, and a specified Wenkebach AF detection threshold, and classify a segment of the cardiac signal sensed prior to the detected episode as AF when using a change in one or more of the specified V-V interval dispersion threshold, the specified V-V interval double decrement threshold, and the specified Wenkebach AF detection threshold.

In Example 6, the subject matter of one or any combination of Examples 1-5 optionally includes an arrhythmia detection circuit configured to detect the episode of AF when noise in the sensed cardiac signal is less than a specified noise detection threshold, and classify the segment of the cardiac signal sensed prior to the detected episode as AF when noise in the segment satisfies a different noise detection threshold.

In Example 7, the subject matter of one or any combination of Examples 1-6 optionally includes an arrhythmia detection circuit configured to apply the first AF detection to the sensed cardiac signal according to sensing windows and count a number of the sensing windows in which AF is detected as the time duration of the AF episode, and add a sensing window prior to a first sensing window in which AF is detected to the count of the number of sensing windows when AF is detected in the prior sensing window using the different AF detection criteria.

In Example 8, the subject matter of one or any combination of Examples 1-7 optionally includes a control circuit configured to trigger storage of sampled values of a segment of the sensed cardiac signal that includes the detected episode of AF when the episode of AF is detected using the first AF detection criteria, and trigger storage of sampled values of a segment of the cardiac signal that includes both the detected episode of AF and the sensed cardiac signal prior to the detected episode of AF when AF is detected in the prior sensed cardiac signal.

In Example 9, the subject matter of one or any combination of Examples 1-8 optionally includes an arrhythmia detection circuit is configured to accumulate a plurality of detected episodes of AF into a total time of AF burden for the subject and generate an alert according to the total time of AF burden.

In Example 10, the subject matter of one or any combination of Examples 1-9 optionally includes a therapy circuit configured to provide electrical pacing therapy to the subject; and a control circuit configured to initiate delivery of the electrical pacing therapy according to a first pacing therapy mode, and change the pacing therapy mode according to the value of total time duration of the detected AF episode.

In Example 11, the subject matter of one or any combination of Examples 1-10 optionally includes a therapy circuit configured to provide defibrillation shock therapy to the subject; and a control circuit configured to initiate delivery of the defibrillation shock therapy when the total time duration of the detected AF episode exceeds a specified time duration threshold.

In Example 12, the subject matter of one or any combination of Examples 1-11 optionally includes an arrhythmia detection circuit configured to generate an indication of the start time of the episode of arrhythmia when the episode of arrhythmia is detected in the prior sensed cardiac signal.

Example 13 includes subject matter (such as a method of operating an ambulatory medical device, a means for performing acts, or a machine-readable medium including instructions that, when performed by the machine, cause the machine to perform acts), or can optionally be combined with one or any combination of Examples 1-12 to include such subject matter, comprising sensing a cardiac signal representative of cardiac activity of a subject; detecting an episode of cardiac arrhythmia in the sensed cardiac signal using one or more first arrhythmia detection criteria and timing the duration of the arrhythmia episode; applying, when the episode of arrhythmia is detected, different one or more arrhythmia detection criteria to a duration of the sensed cardiac signal prior to the detected episode of arrhythmia; adding the duration of the prior sensed cardiac signal to the time duration of the arrhythmia episode when arrhythmia is detected in the prior sensed cardiac signal using the different arrhythmia detection criteria; and providing the total time duration of the detected arrhythmia episode to a user or process.

In Example 14, the subject matter of Example 13 optionally includes detecting an episode of atrial fibrillation (AF) in the sensed cardiac signal using one or more first AF detection criteria and timing the duration of the AF episode, wherein the applying the different arrhythmia detection criteria includes applying different one or more AF detection criteria to a duration of the sensed cardiac signal prior to the detected episode of AF when the episode of AF is detected.

In Example 15, the subject matter of Example 14 optionally includes the one or more first AF detection criteria including a plurality of AF detection criteria having first specificity and first sensitivity to detection of AF, and wherein the different one or more AF detection criteria includes a subset of the first AF detection criteria with at least one of different specificity or different sensitivity than the first AF detection criterion.

In Example 16, the subject matter of one or both of Examples 14 and 15 optionally includes the one or more first AF detection criteria including detecting when sensed ventricular depolarization intervals (V-V intervals) satisfy one or more of a specified V-V interval dispersion threshold, a specified V-V interval double decrement threshold, and a specified Wenkebach AF detection threshold, and wherein the different one or more AF detection criteria includes a change in one or more of the specified V-V interval dispersion threshold, the specified V-V interval double decrement threshold, and the specified Wenkebach AF detection threshold.

In Example 17 the subject matter of one or any combination of Examples 13-16 optionally includes the one or more first AF detection criteria including detecting when noise in the sensed cardiac signal is less than a specified noise detection threshold, and wherein the different one or more AF detection criteria includes detecting when noise in the sensed cardia signal is less than a different specified noise detection threshold.

In Example 18, the subject matter of one or any combination of Examples 13-17 optionally includes detecting the episode of AF during a first sensing window, wherein the timing the duration of the AF window includes counting a number of sensing windows with the AF episode, and wherein the adding the duration of the prior sensed cardiac signal to the AF episode includes adding a sensing window prior to the first sensing window to the count of the number of sensing windows with the AF episode.

Example 19 includes subject matter (such as a system), or can optionally be combined with one or any combination of Examples 1-18 to include such subject matter, comprising: an implantable cardiac lead including one or more implantable electrodes; a cardiac signal sensing circuit operatively coupled to the electrodes and configured to provide a sensed ventricular cardiac signal of a subject; and an arrhythmia detection circuit operatively coupled to the cardiac signal sensing circuit and configured to: detect an episode of atrial fibrillation (AF) in the sensed ventricular cardiac signal in absence of dedicated atrial chamber sensing using one or more first AF detection criteria, and begin timing the duration of the AF episode; apply different AF detection criteria to a duration of the sensed cardiac signal prior to the detected episode of AF when the episode of AF is detected;

add the duration of the prior sensed cardiac signal to the time duration of the AF episode when AF is detected in the prior sensed cardiac signal using the different AF detection criteria; and generate a value of total time duration of the detected AF episode.

In Example 20, the subject matter of Example 19 optionally includes an arrhythmia detection circuit configured to detect the episode of AF using a plurality of AF detection criteria to the sensed cardiac signal having first specificity and first sensitivity to AF detection, and apply a subset of the first AF detection criteria to a segment of the cardiac signal sensed prior to the detected episode of AF with at least one of different specificity or different sensitivity than the first AF detection criterion.

In Example 21, the subject matter of one or both of Examples 19 and 20 optionally includes an arrhythmia detection circuit configured to detect the episode of AF when sensed ventricular depolarization intervals (V-V intervals) satisfy one or more of a specified V-V interval dispersion threshold, a specified V-V interval double decrement threshold, and a specified Wenkebach AF detection threshold, and classify a segment of the cardiac signal sensed prior to the detected episode as AF when using a change in one or more of the specified V-V interval dispersion threshold, the specified V-V interval double decrement threshold, and the specified Wenkebach AF detection threshold.

In Example 22, the subject matter of Example 21 optionally includes an arrhythmia detection circuit configured to detect the episode of AF when noise in the sensed cardiac signal is less than a specified noise detection threshold, and classify the segment of the cardiac signal sensed prior to the detected episode as AF when noise in the segment satisfies a different noise detection threshold.

Example 23 can include, or can optionally be combined with any portion or combination of any portions of any one or more of Examples 1-22 to include, subject matter that can include means for performing any one or more of the functions of Examples 1-22, or a machine-readable medium including instructions that, when performed by a machine, cause the machine to perform any one or more of the functions of Examples 1-22.

These non-limiting examples can be combined in any permutation or combination. This section is not intended to provide an exclusive or exhaustive explanation of the invention. The detailed description is included to provide further information about the present patent application such as a discussion of the dependent clams and the interrelation of the dependent and independent claims.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other ambulatory device need not include all of the features described herein, but may be implemented to include selected features that provide for unique structures or functionality. Such a device may be implemented to provide a variety of therapeutic or diagnostic functions.

Figure 1:
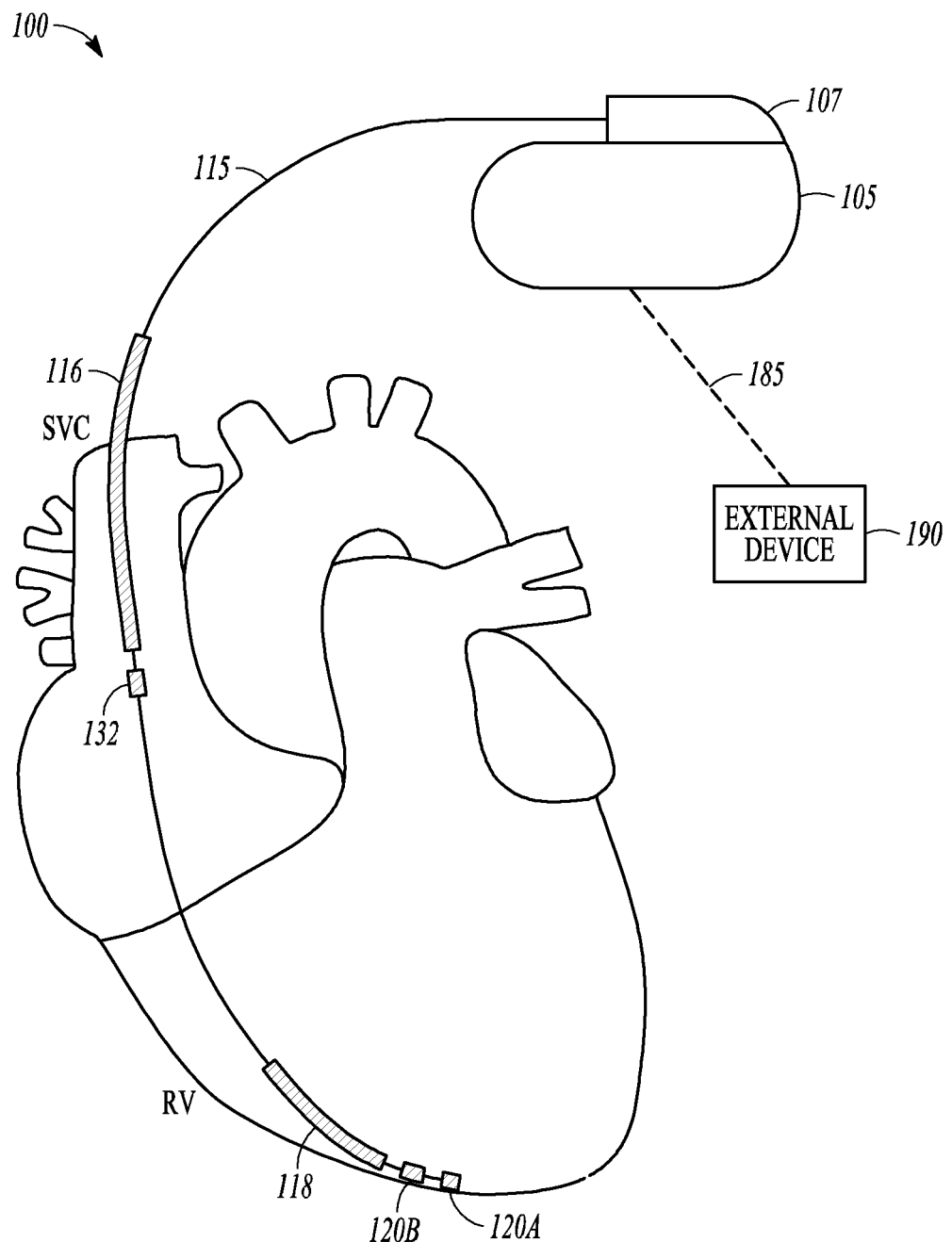
FIG. 1 is an illustration of an example of portions of a medical device system that includes an IMD.

FIG. 1 is an illustration of an example of portions of a system 100 that includes an ambulatory medical device that is an IMD 105. Examples of the IMD 105 include, without limitation, a pacemaker, a cardioverter, a defibrillator, and other cardiac monitoring and therapy delivery devices, including cardiac devices that include or work in coordination with one or more neuro-stimulating devices, drugs, drug delivery systems, or other therapies. In an example, the system 100 shown is used to treat cardiac arrhythmias. The IMD 105 typically includes an electronics unit coupled by one or more cardiac leads 115 to a heart of a patient or subject. The electronics unit of the IMD 105 typically includes components that are enclosed in a hermetically-sealed housing sometimes referred to as a canister or "can." The system 100 also typically includes an IMD programmer or other external system 190 that communicates one or more wireless signals 185 with the IMD 105, such as by using radio frequency (RF) or by one or more other telemetry methods.

The example shown includes a right ventricular (RV) lead 115 having a proximal end and a distal end. The proximal end is coupled to a header connector 107. The distal end is configured for placement in the RV. The RV lead 115 can include one or more of a proximal defibrillation electrode 116, a distal defibrillation electrode 118 (e.g., RV Coil), an RV tip electrode 120A, and an RV ring electrode 120B. The defibrillation electrode 116 is generally incorporated into the lead body such as in a location suitable for supraventricular placement in the superior vena cava (e.g., SVC Coil). In some examples, the RV lead 115 includes a ring electrode 132 (e.g., SVC ring) in the vicinity of the proximal defibrillation electrode 116. The defibrillation electrode 118 is incorporated into the lead body near the distal end, such as for placement in the RV. The RV electrodes 120A and 120B can form a bipolar electrode pair and are generally incorporated into the lead body at the lead distal end. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart. The RV tip electrode 120A, RV ring electrode 120B, or an electrode formed on the can of IMD 105 allow for sensing an RV electrogram signal representative of RV depolarizations and delivering RV pacing pulses. The 1 MB 105 includes a sense amplifier circuit to provide amplification or filtering of the sensed signal. Sensing and pacing allows the 1 MB 105 to adjust timing of the heart chamber contractions.

Some IMDs, such as shown in FIG. 1, may not include any electrodes for sensing electrical activity in an atrium. For example, the 1 MB 105 can be an ICD with single ventricular chamber sensing. The ICD can include an electrode attached to a single ventricular lead, and use intrinsic cardiac signals sensed with the ventricular electrode for arrhythmia detection and discrimination (e.g., by rate sensing and/or depolarization signal morphology analysis).

An IMD may be a diagnostic-only device that does not provide electrical therapy to the patient. Note that the specific arrangement of leads and electrodes are shown the illustrated example of FIG. 1 is intended to be non-limiting.

Figure 2:
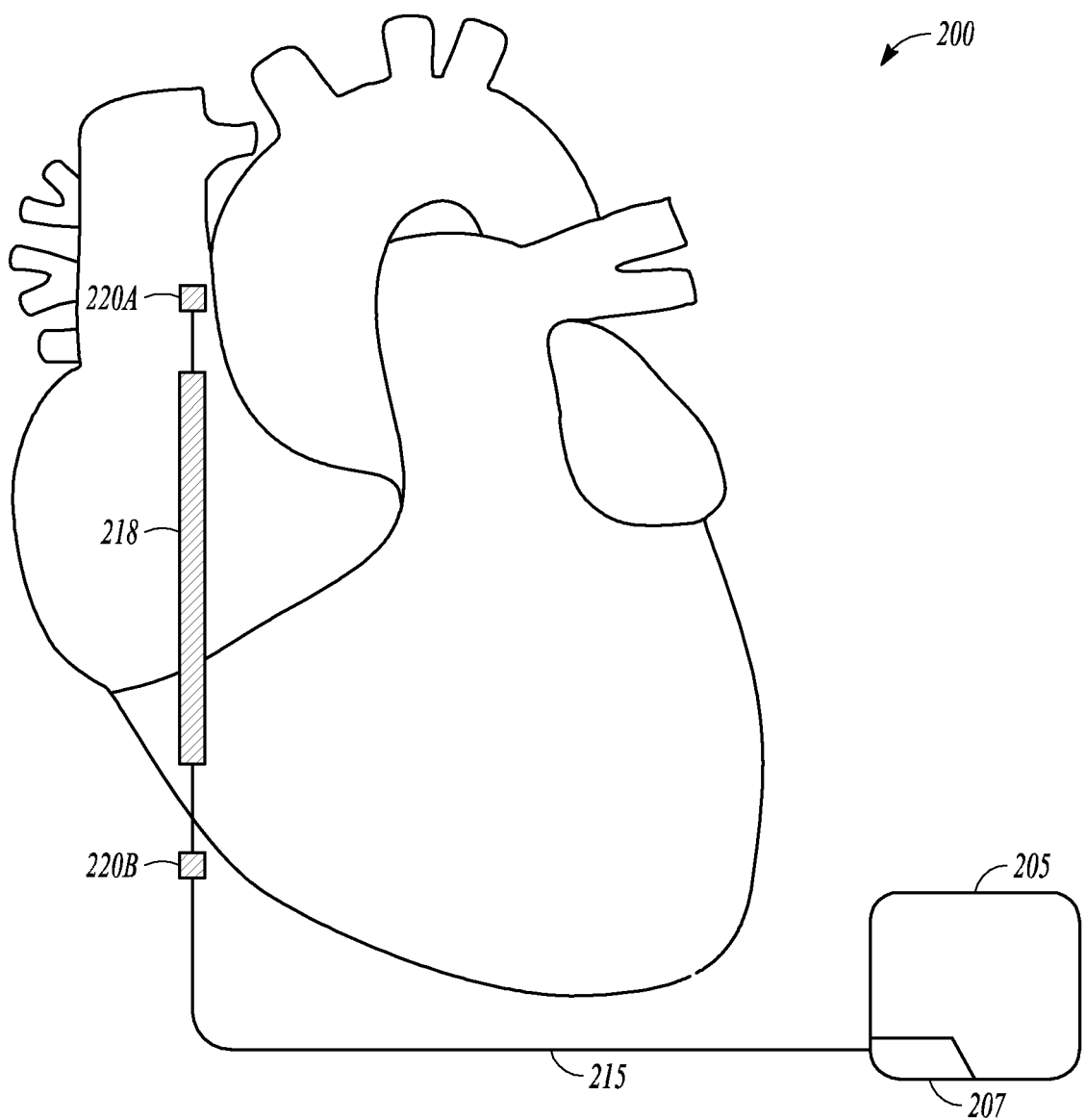
FIGS. 2 and 3 are illustrations of further examples of an IMD.

FIG. 2 is an illustration of another example of portions of a system 200 that includes an S-ICD 205. The S-ICD 205 is implantable subcutaneously and includes a lead 215. The lead 215 is implanted subcutaneously and the proximal end of the lead 215 is coupled to a header connector 207. The lead 215 can include electrode 220A and electrode 220B to sense ventricular depolarization (e.g., using far-field sensing), but in the example illustrated, the lead does not include any electrodes that directly contact the heart. The lead 215 includes a defibrillation electrode 218 that may be a coil electrode. The S-ICD 205 may provide one or more of cardioversion therapy and defibrillation high energy shock therapy to the heart using the defibrillation electrode 218 and an electrode formed on the can of the S-ICD 205. In some examples, the S-ICD 205 may also provide pacing pulses for anti-tachycardia therapy or bradycardia therapy. Note that atrial leads are not provided in the arrangement of the electrodes, but electrodes 220A and 220B allow for sensing a far-field ventricular electrogram signal.

Figure 3:
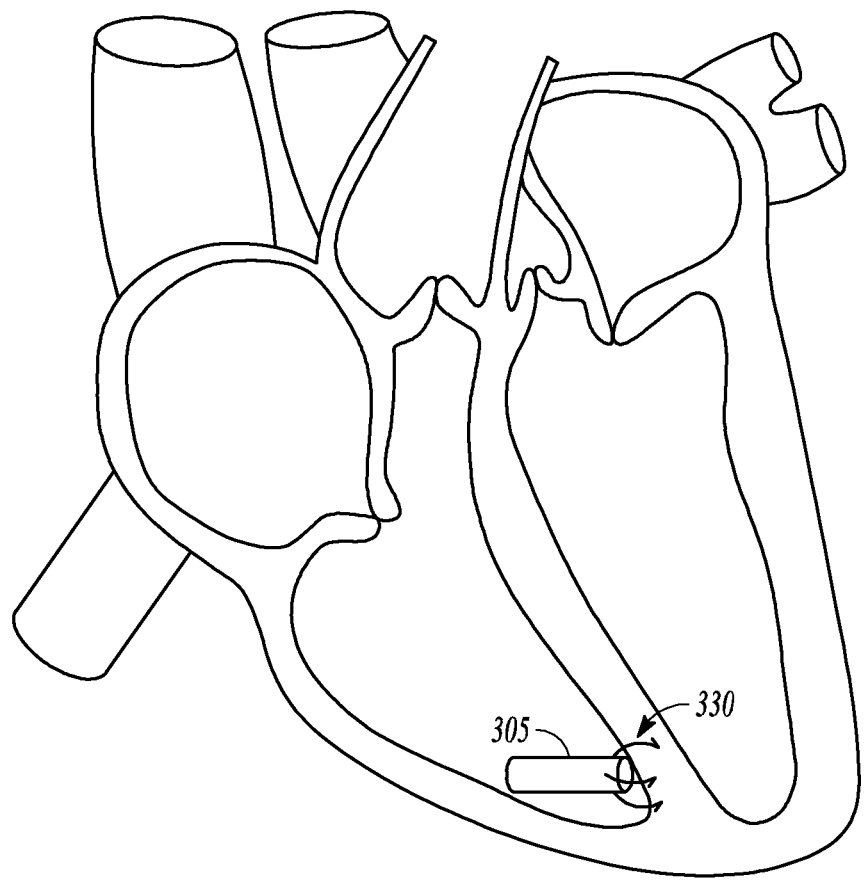

FIG. 3 is an illustration of an example of an IMD that is a leadless cardiac pacemaker 305. The leadless pacemaker 305 is shown positioned within a ventricular chamber, but the leadless pacemaker 305 may be positioned at other locations of the heart. The leadless pacemaker 305 example has a cylindrical housing and may include one or more electrodes arranged along the cylindrical housing to sense electrical signals of the heart and/or provide electrical stimulation for pacing the heart. In some instances the one or more electrodes may be used for communication. The leadless pacemaker 305 may include a mechanism 330 to secure the leadless pacemaker 305 to the heart. Examples of the fixation mechanism can include one or more tines, or one or more helix-shaped fixation mechanisms. In example of FIG. 3, the electrodes may not be in direct contact with the atrium, but the electrodes may provide an RV electrogram signal.

Other examples of an IMD include an implantable cardiac recorder (ICM). The ICM may be a diagnostic device inserted subcutaneously to monitor the electrical signals and, depending on the device, other signals of the heart. The ICM may include two or more electrodes on the housing and/or header of the device to sense the electrical signals of the heart. In some cases, no electrodes are provided in or on the heart.

Figure 4:
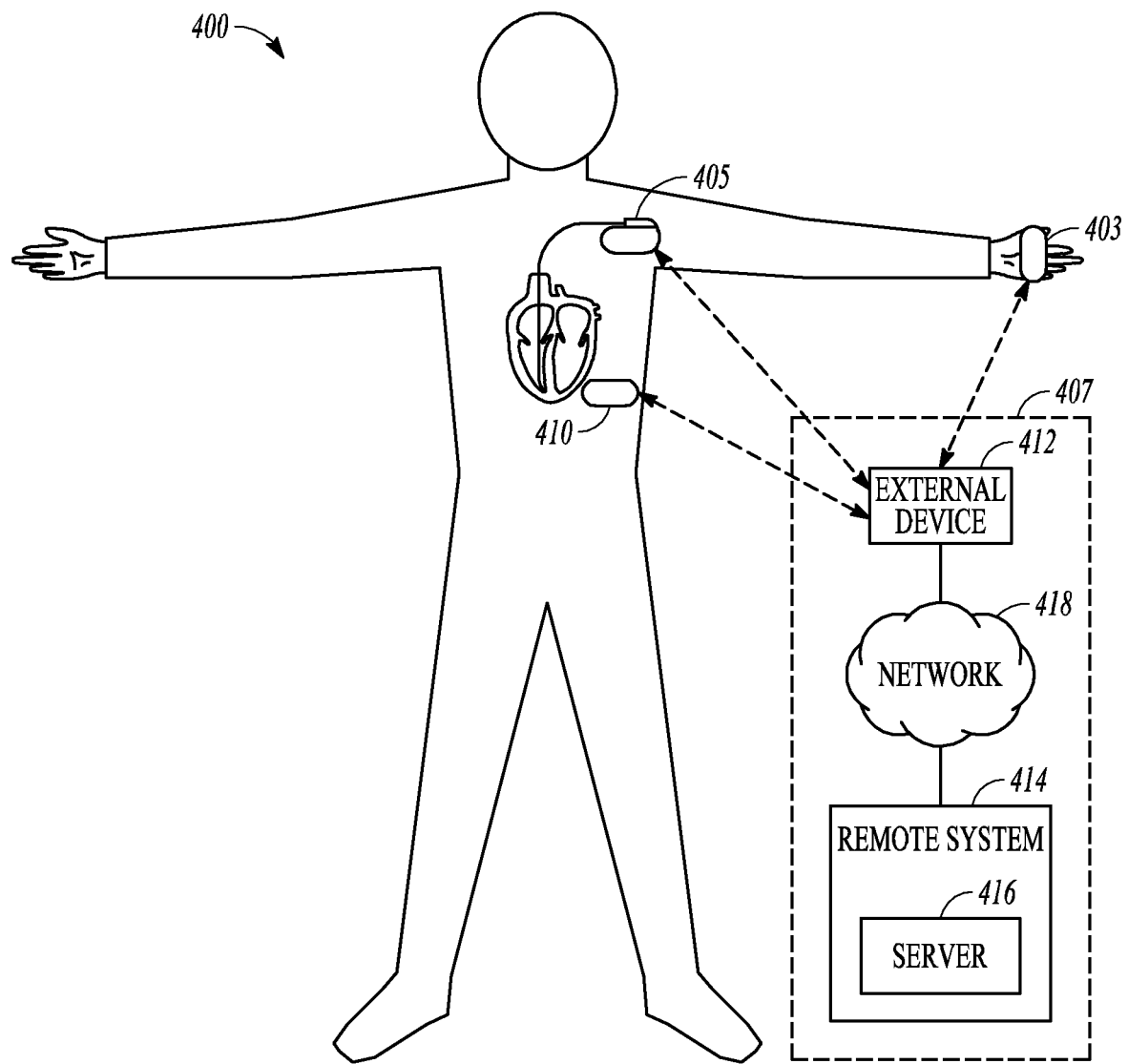
FIG. 4 is an illustration of portions of another example of a medical device system.

FIG. 4 is an illustration of portions of another example of a medical device system 400. The system 400 may include one or more ambulatory medical devices, such as a conventionally implantable or subcutaneously implantable medical device 405, a wearable medical device 410, or a handheld medical device 403, or any other medical device described herein. One or more of the medical devices can include a communication circuit (e.g., a telemetry circuit) to communicate an indication of cardiac arrhythmia (e.g., AF) to a communication system 407. The communication system 407 can include an external communication device 412 and a remote system 414 that communicates with the external communication device 412 via a network 418 (e.g., the internet, a proprietary computer network, or a cellular phone network). The remote system 414 may include a server 416 remotely located from the external communication device 412 and the subject to perform further processing of the cardiac data or other patient management functions. The external communication device 412 may include a programmer to program parameters of the implantable medical device. One or both of the external communication device 412 and the remote system 414 may include a display to present the indication of arrhythmia to a user, such as a clinician.

Figure 5:
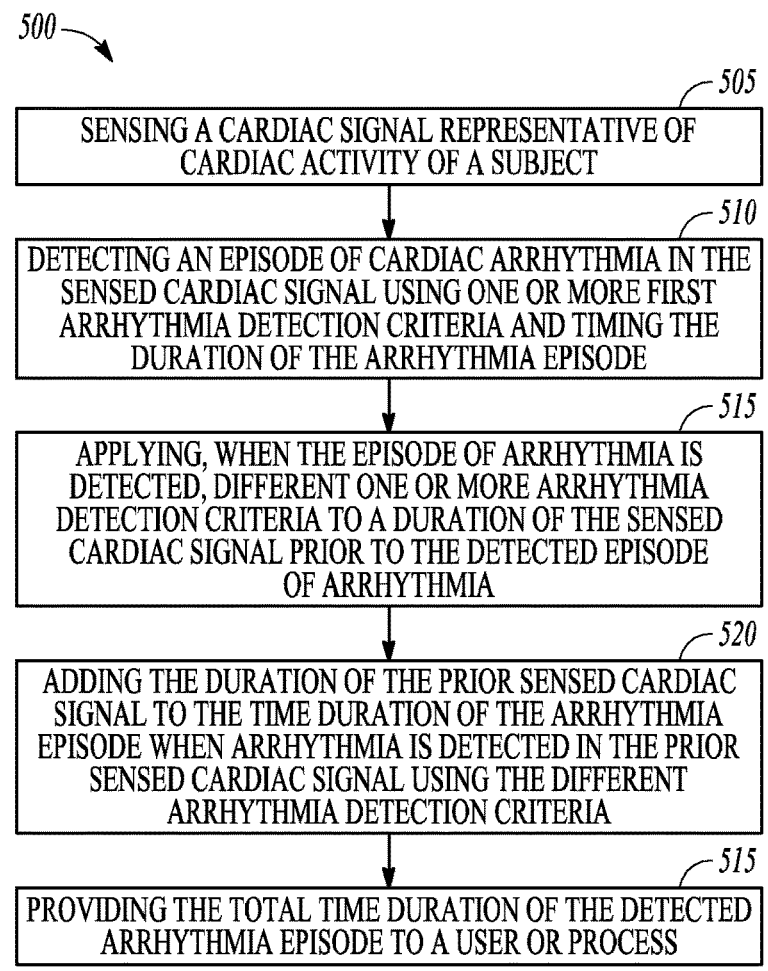
FIG. 5 is a flow diagram of an example of a method of operating an ambulatory medical device.

FIG. 5 is a flow diagram of an example of a method 500 of controlling operation of an ambulatory medical device system to detect atrial arrhythmias. At 505, a cardiac signal representative of cardiac activity of a subject is sensed by the device. At 510, an episode of atrial arrhythmia (e.g., AF) is detected in a first portions of the sensed cardiac signal using one or more first arrhythmia detection criteria, and the medical device begins timing the duration of the detected arrhythmia episode.

At 515, upon detection of the episode of atrial arrhythmia using the first detection criteria, the device analyzes a duration of the cardiac signal sensed prior to the detected episode of arrhythmia using a different arrhythmia detection criterion or criteria. The different detection criteria for the arrhythmia may change one or both of the sensitivity and specificity of the arrhythmia detection from the first criteria. Sensitivity refers to the ability of the detection scheme of a device to effectively detect an abnormal heart rhythm that the device may treat. Specificity refers to the ability of the detection scheme of a device to correctly identify heart rhythm that the device is not intended to detect or treat (e.g., normal rhythms, other types of arrhythmias, or noise mistakenly identified as cardiac arrhythmia). As an example, the sensitivity of the arrhythmia detection may be changed to be more inclusive of possible arrhythmia in the signal segment prior to the detected episode. The prior signal segment may be sampled and stored in a memory buffer of the device (e.g., as an electrogram), and the second detection criteria is applied to the stored segment.

At 520, the ambulatory medical device adds the duration of the prior sensed cardiac signal to the time duration of the arrhythmia episode when arrhythmia is detected in the prior sensed cardiac signal using the different arrhythmia detection criteria. Accuracy of the device-determined total time of the arrhythmia episode can be improved by this "look-back" feature that checks whether episodes of arrhythmia were missed by the first detection criteria. At 525, the device provides the duration of the detected arrhythmia episode to a user or process.

In some examples, the ambulatory medical device detects AF in the sensed cardiac signal using first AF detection criteria and begins timing the AF episode. The device then applies different AF detection criteria to the duration of the sensed cardiac signal prior to the detected episode of AF. When AF is detected in the prior signal segment, the duration of the prior episode can be added to the total time of the AF episode. In this way, the device may detect missed episodes of AF that can be included in the total time of the AF episodes to improve determination of AF burden for the patient or subject.

Additionally, the ambulatory medical device may store electrograms or ECGs of detected arrhythmia episodes. The look-back feature allows for the prior signal segment to be included in the stored electrogram or ECG to be later uploaded from the device for analysis by a clinician if the arrhythmia is detected in the prior segment. The look-back feature may prevent the additional information from being lost or ignored.

The additional information obtained can be reviewed by a clinician and used to adjust a treatment of the patient. This adjusting can include adjusting drug titration, changing the drug used in the therapy, prescribing an implantable medical device for the patient, adjusting the therapy (e.g. electrostimulation therapy) of an implantable device prescribed to the patient, or ordering an ablation procedure for the patient.

Figure 6:
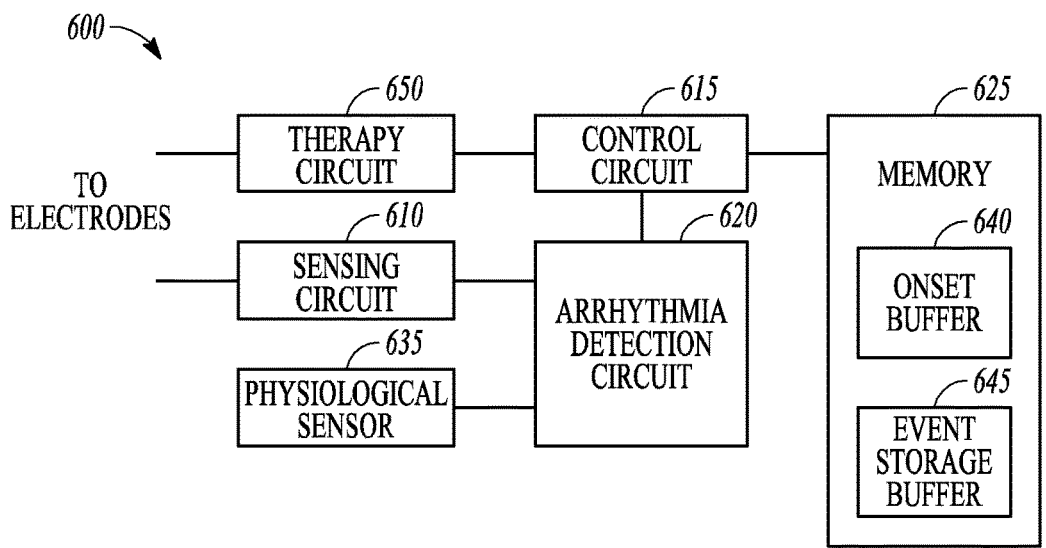
FIG. 6 shows a block diagram of portions of an example of an ambulatory medical device.

FIG. 6 is a block diagram of portions of an example of an ambulatory medical device. The device 600 includes a sensing circuit 610, a control circuit 615, an arrhythmia detection circuit 620, and may include a memory 625. The sensing circuit 610 may generate a sensed cardiac signal representative of cardiac activity of a subject. In certain examples, the sensing circuit 610 may be electrically coupled to one or more implantable electrodes included in a lead arranged for placement in a heart chamber. In certain examples, the sensing circuit 610 may be electrically coupled to one or more implantable electrodes included in a leadless implantable medical device. In certain examples, the sensing circuit 610 may be electrically coupled to one or more implantable electrodes configured to sense cardiac signals without direct cardiac contact with the subject (e.g., a subcutaneously implantable electrode). In certain examples, the sensing circuit 610, the control circuit 615, the arrhythmia detection circuit 620, and the memory 625 are included in a wearable device or a handheld device. In variations the memory can be included in a separate device or can be a central memory located in a network "cloud."

The control circuit 615 may include a microprocessor, a digital signal processor, application specific integrated circuit (ASIC), or other type of processor, interpreting or executing instructions included in software or firmware. The memory 625 may be integral to or separate from the control circuit 615. The arrhythmia detection circuit 620 may also be integral to the control circuit 615 or may be separate from the control circuit 615. In certain examples, the sensing circuit 610 is included in a first device and the arrhythmia detection circuit and the control circuit are included in a second separate device. In certain examples, the first device is implantable and the second devices is external.

The arrhythmia detection circuit 620 may detect an episode of cardiac arrhythmia in the sensed cardiac signal using one or more arrhythmia detection criteria. For instance, the arrhythmia detection circuit 620 may be configured to detect AF. In some examples, the arrhythmia detection circuit 620 uses ventricular depolarization (V-V) interval dispersion to detect AF.

Figure 7:
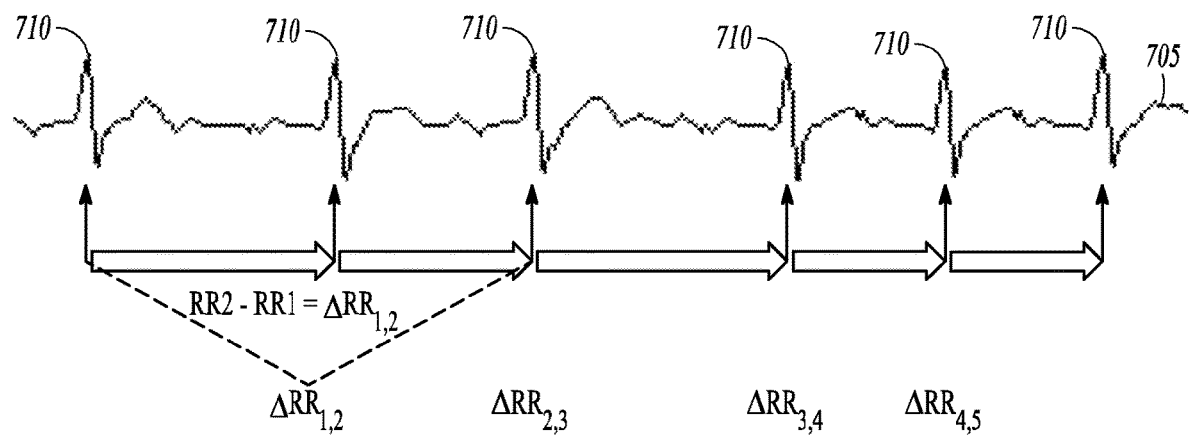
FIG. 7 shows a representation of a sensed cardiac signal.

FIG. 7 shows a representation of a sensed cardiac signal 705. The sensed signal is shown having a number of R-waves 710. The V-V intervals can be determined as intervals between R-waves. RR1 in the Figure refers to the first interval between the first two R-waves; RR2 is the second interval between the second R-wave and the third R-wave, and so on. Differences between the V-V intervals are referred to $\Delta RR_{1,2}$ (e.g., the difference between the RR2 and RR1), $\Delta RR_{2,3}$ and so on.

Figure 8:
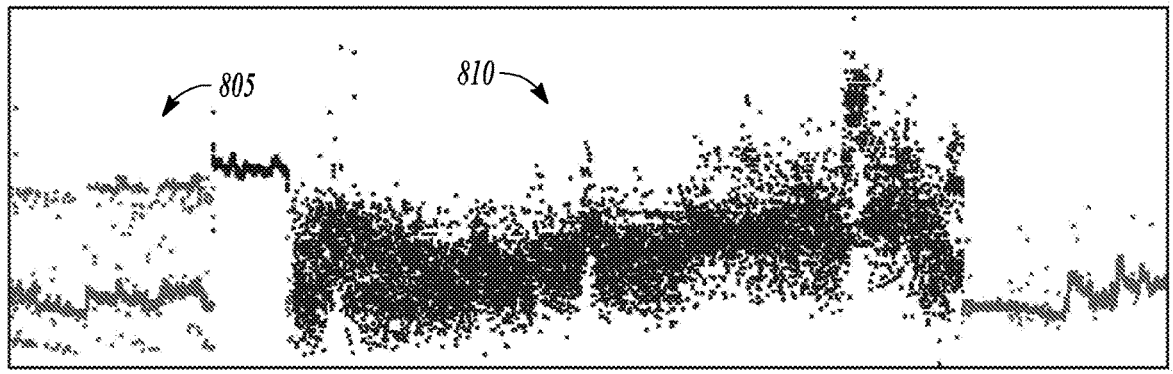
FIG. 8 shows an example of a sensed physiological signal having both normal sinus rhythm and atrial fibrillation.

FIG. 8 shows an example of a sensed physiological signal having a first region 805 corresponding to NSR and a second region 810 corresponding to AF. In the NSR region, the V-V intervals may be more regular and the differences in the V-V intervals will be small. In the AF region, the V-V intervals may be more disperse and the values of the differences in the V-V intervals may be more varied than for NSR. The arrhythmia detection circuit 620 may include a peak detector circuit to detect R-waves in the sensed physiological signal to determine V-V intervals. The arrhythmia detection circuit 620 may sample the V-V intervals and store the samples in device memory 625 or a different memory. The arrhythmia detection circuit 620 may determine differences between the V-V intervals and determine a measure of V-V interval dispersion using the determined V-V interval differences.

In some examples, the arrhythmia detection circuit 620 determines the differences in the V-V intervals and may classify the interval differences as one of stable or unstable. The interval difference classifications can be used to determine V-V interval dispersion. An interval difference may be classified as stable when the interval difference is less than a specified threshold difference value from an immediately previous interval difference. An interval difference may be classified as unstable when the interval difference is more than the specified threshold difference value from the immediately previous interval difference. As an illustrative example intended to be non-limiting, the threshold difference value is a value corresponding to less than a 10 bpm difference in rate between the two intervals. Thus, if RR2 in FIG. 7 is 1000 ms corresponding to 60 bpm, and RR1 is 857 ms corresponding to 70 bpm, the interval difference $\Delta RR_{1,2}$ is classified as stable. If RR1 is less than 857 ms, then the interval difference is classified as unstable.

In the example of FIG. 8, more of the V-V interval differences will be stable in the NSR region. In the AF region, the number of unstable V-V interval differences will increase relative to the number of stable V-V interval differences. The arrhythmia detection circuit 620 may determine a ratio using a number of stable interval differences and a number of unstable interval differences (e.g., ratio=unstable/stable). The arrhythmia detection circuit 620 may detect AF when the ratio exceeds an AF detection threshold ratio.

In another example, the arrhythmia detection circuit 620 detects AF when sensed V-V intervals satisfy a specified V-V interval double decrement threshold.

An interval double decrement occurs when two consecutive V-V intervals occur in which heart rate decreases in both intervals. In the example of FIG. 7, if RR1 is 857 ms corresponding to 70 bpm and RR2 is 1000 ms corresponding to 60 bpm, a double decrement occurs if the next interval RR3 is greater than 1000 ms (e.g., 1090 ms corresponding to the 55 bpm). If RR3 is less than 1000 ms, heart rate did not decrease in two consecutive V-V intervals and a double decrement did not occur. The arrhythmia detection circuit may detect AF when the number of double decrement intervals exceeds a specified fraction or percentage of the intervals. Premature atrial contractions (PACs) can cause false positives in AF detection schemes. Including the double decrement detection criterion in an AF detection scheme can reduce false positives. The threshold fraction or percentage can be lowered to make the detection more sensitive or raised to make the detection more specific for AF detection.

In another example, the arrhythmia detection circuit 620 detects AF when sensed V-V intervals satisfy a specified V-V interval Wenkebach threshold. Wenkebach detection involves an analysis of how truly irregular is an arrhythmia that first appears to be irregular, but may actually include some regularity or pattern. The arrhythmia detection circuit 620 may detect AF when the measured Wenkebach regularity of the rhythm is less than a specified Wenkebach threshold. For instance, measuring the regularity may include determining one or both of similar maximum heart rate and similar minimum heart rate. The arrhythmia detection circuit 620 may look for a consecutive number of X-beat windows in the sensed cardiac signal, where X is a positive integer greater than one (e.g., 2, 3 . . . or 7 beat windows). Multiple different window sizes are applied to the sensed cardiac signal. The arrhythmia detection circuit 620 determines the highest percentage of X-beat windows with similar maximum heart rates (and/or similar minimum heart rates).

Table I is an illustrative example of window sizes of X=2 to 7 beats and a percentage of consecutive X-beat widows that had similar maximum or minimum heart rate. A "similar" maximum or minim heart rate means that the max (or min) for a given window is within, as an example, +/−5 bpm of the previous window max (or min).

TABLE I

| Window-size | % Max HR | % Min HR |
| --- | --- | --- |
| 2 | 20% | 25% |
| 3 | 31% | 36% |
| 4 | 42% | 47% |
| 5 | 53% | 58% |
| 6 | 64% | 69% |
| 7 | 75% | 80% |

If any of the window sizes includes a fraction or percentage of maximum heart rate (or minimum heart rate) that exceeds the specified Wenkebach threshold, the arrhythmia detection circuit 620 does not detect AF. If the fraction or percentage of maximum heart rate (and/or minimum heart rate) of all of the window sizes are less than the specified Wenkebach threshold, the arrhythmia detection circuit 620 detects AF. In the example of Table I, 20% of the consecutive 2-beat windows had a similar maximum heart rate and 25% had a similar minimum heart rate, and 75% of the consecutive 7-beat windows had similar maximum heart rates and 80% had similar minimum heart rates. If the Wenkebach threshold percentage is specified as 40%, the arrhythmia detection circuit 620 would not detect AF in the example. Any of window sizes 4 through 7 would negate a finding of AF because a repeating pattern is found for those window sizes that meets the Wenkebach detection criterion. The threshold fraction or percentage can be raised to make the detection more sensitive or lowered to make the detection more specific for AF detection.

In another example, the arrhythmia detection circuit 620 uses an analysis of morphology of the sensed cardiac signal to detect AF. The arrhythmia detection circuit 620 may include a correlation module that determines a score associated with correlation of the morphology of the sensed cardiac signal to the morphology of a template signal representative of AF. An example of a correlation score is a feature correlation coefficient (FCC). The FCC can provide an indication of a degree of similarity between the shape of the sensed electrogram and the shape of the template electrogram signal that represents AF. The template may be recorded for a particular subject or may be created based on a patient population. An approach to calculating a correlation score can be found in U.S. Pat. No. 7,904,142, titled "Self-Adjusting; ECG Morphological Feature Correlation Threshold," filed May 16, 2007, which is incorporated herein by reference in its entirety. The arrhythmia detection circuit 620 may detect AF when the determined score satisfies a specified AF detection threshold. The detection for AF can be adjusted to be more sensitive or less sensitive by adjusting the threshold score.

Figure 9:
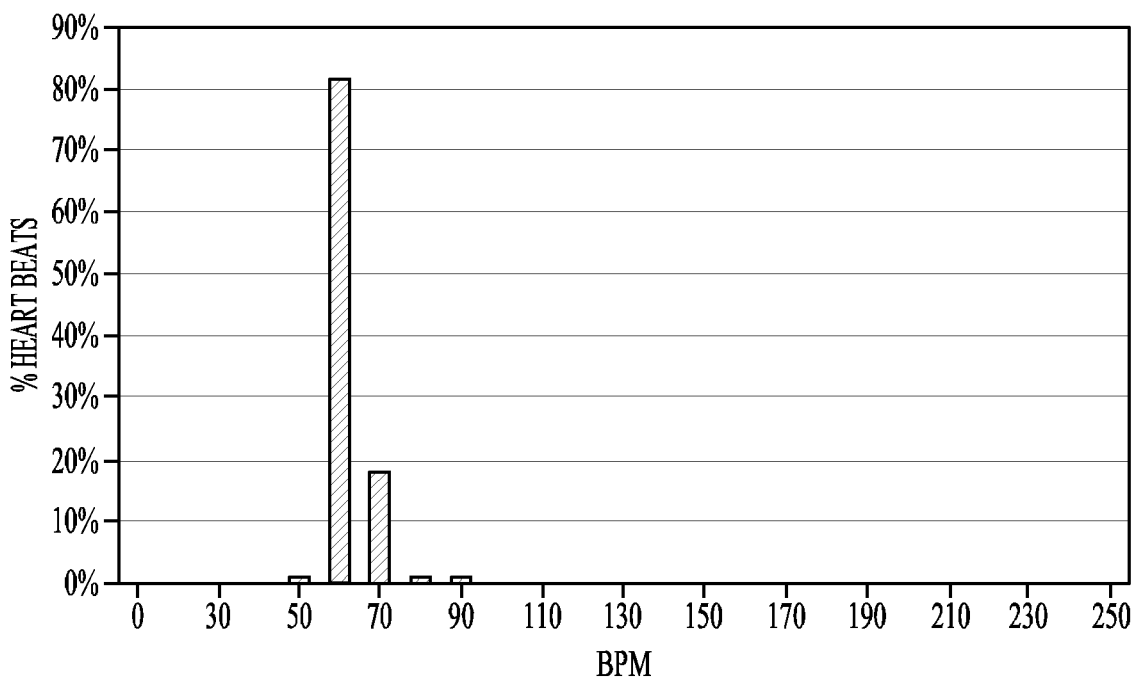
FIG. 9 shows a graph of an example of a heart rate distribution for normal sinus rhythm.
Figure 10:
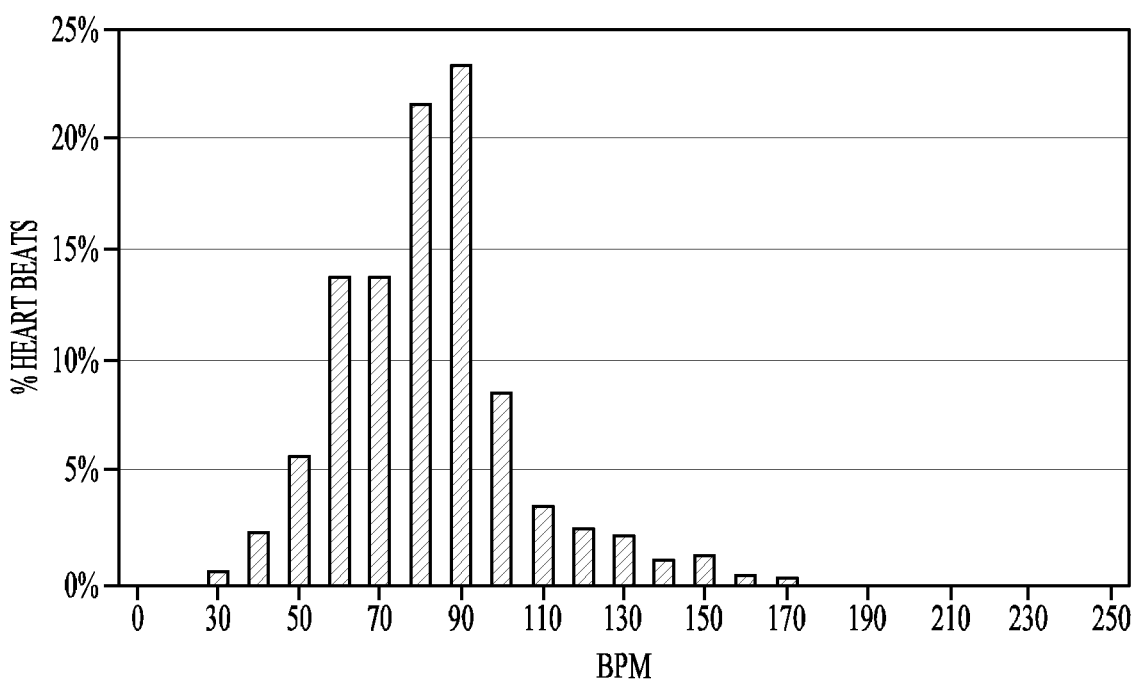
FIG. 10 shows a graph of an example of a heart rate distribution for a patient in atrial fibrillation.

In another example, the arrhythmia detection circuit 620 determines a V-V interval distribution using sampled V-V interval values and determines a heart rate density index (HRDI) as a portion of the sampled V-V interval values corresponding to a V-V interval occurring most often in the distribution. FIG. 9 shows a graph of an example of a heart rate distribution for normal sinus rhythm (NSR). Alternatively, the distribution may be a V-V interval distribution. Most of the samples of the distribution are located between approximately 50 bpm and 90 bpm. In some variations, HRDI can be expressed as a fraction (e.g., a percentage) of the intervals. In the example of FIG. 9, the HRDI is 81% corresponding to the heart rate mode of 60 bpm. FIG. 10 shows a graph of an example of a heart rate distribution for a patient in AF. It can be seen that heart rate is less regular in AF than in NSR. In the example of FIG. 10, the HRDI is approximately 23%. AF can be detected when the HRDI is less than a specified detection threshold fraction or percentage. The detection for AF can be adjusted to be more sensitive or less sensitive by adjusting the detection threshold.

The arrhythmia detection circuit 620 may also use noise analysis when detecting arrhythmia to discriminate the arrhythmia from noise. In certain examples, the medical device includes one or more filter circuits and the arrhythmia detection circuit detects noise according to the energy of the sensed cardiac signal present above a specified noise frequency. In certain examples, noise is detected in the sensed cardiac signal using a morphology analysis of the signal. In some examples, one or more AF detection criteria are applied to a detection window of a specified size (e.g., a two-minute window). The arrhythmia detection circuit 620 may require that signal noise in the detection window be less than a specified noise detection threshold when detecting AF. For instance, the arrhythmia detection circuit 620 may require that the number of noise hits detected during the detection window be less than a specified threshold number of noise hits.

When AF is detected, the control circuit 615 may begin timing the duration of the arrhythmia episode. A determination of the total time that the subject is in AF (the AF burden) can be impacted when AF detection thresholds are applied to an atrial rhythm that is fluctuating around the AF detection thresholds. The medical device may be configured to detect AF using one or more criteria that may miss arrhythmias that belong to the AF episode.

According to some examples, when the episode of AF is detected the arrhythmia detection circuit 620 applies different AF detection criteria to a duration of the sensed cardiac signal prior to the detected episode of AF. If AF is detected in the non-AF window using the different AF detection criteria, the device adds the duration of the detection window to the total time duration of the detected arrhythmia episode. This may allow detection of AF that was missed by the first detection criteria and may provide a more accurate assessment of the duration of the AF episode.

In some examples, the arrhythmia detection circuit 620 first detects the episode of AF from the sensed cardiac signal using AF detection criteria that has first specificity and first sensitivity to AF detection. The arrhythmia detection circuit 620 then changes the AF detection criteria by changing at least one of the specificity or sensitivity of the detection of one or more of the AF detection criteria.

For instance, the arrhythmia detection circuit 620 may first detect an episode of AF using a combination of measurements of V-V interval dispersion, V-V interval double decrement, V-V interval Wenkebach regularity, and noise obtained from the sensed cardiac signal. The arrhythmia detection circuit 620 may then change the V-V interval dispersion detection to be more sensitive to AF (e.g., by reducing the AF detection threshold for a ratio of dispersion), and may change the V-V interval double decrement, and V-V interval Wenkebach regularity to be more specific to AF (e.g., by increasing the double decrement detection threshold, and decreasing the Wenkebach AF detection threshold). The arrhythmia detection circuit may also change the noise threshold for the second AF detection to accept more noise in the signal. The changed detection criteria is applied to the duration of the cardiac signal sensed prior to the detected AF episode.

In certain examples, all of the detection thresholds can be made more sensitive to detect more AF, or can be made more specific to be more discriminatory in what is classified as AF. In certain examples, the look-back criteria is determined using the normal sinus rhythm (NSR) of the subject as a baseline. When AF is detected using the initial AF detection criteria, the arrhythmia detection circuit 620 sets the threshold in the look-back detection criteria to be between the value used in the initial AF detection and the value when the subject is in NSR.

In some examples, the arrhythmia detection circuit 620 first detects the episode of AF from the sensed cardiac signal using a first combination of AF criteria, and then changes the AF detection by changing the combination. For instance, the first AF detection criteria can include one or any combination of a V-V interval dispersion measurement, a V-V interval double decrement measurement, Wenkebach detection, an HRDI measurement, morphology analysis, and noise analysis. The second AF detection criteria includes a different combination of V-V interval dispersion measurements, V-V interval double decrement measurements, Wenkebach detection, HRDI measurements, morphology analysis, and noise analysis.

As explained previously herein, the cardiac signal sensing circuit may not include dedicated sensing circuits for the atrial chambers of the subject. The AF detection is applied to a cardiac signal sensed by a ventricular sensing circuit or circuits. The device-based AF detection methods of measuring V-V interval dispersion, detection of V-V interval double-decrements, measuring V-V interval Wenkebach regularity, measuring HRDI, and performing morphology analysis can be implemented with only ventricular sensing. In this way, AF can be detected without including dedicated atrial sensing in the ambulatory medical device. If atrial sensing circuits are available, other criterion can be used for the AF detection.

Figure 11:
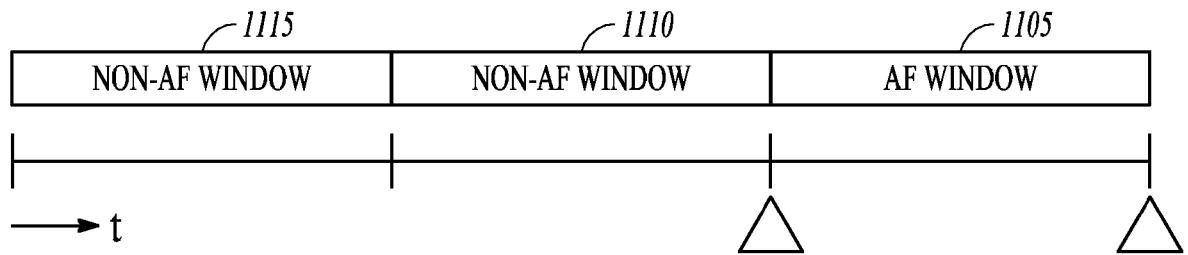
FIG. 11 is an illustration of an example of arrhythmia detection windows.

As explained previously, the arrhythmia detection circuit 620 may apply the AF detection to a specified AF detection window (e.g., a two minute window). FIG. 11 is an illustration of an example of detection windows including an AF window 1105. If AF window 1105 is not too noisy, the arrhythmia detection circuit 620 applies the look-back AF detection criteria to one or more of the previous non-AF windows 1110 and 1115. More than two non-AF windows may be analyzed. The arrhythmia detection window may count the number of windows with AF to determine the duration of the detected AF episode.

Figure 12:
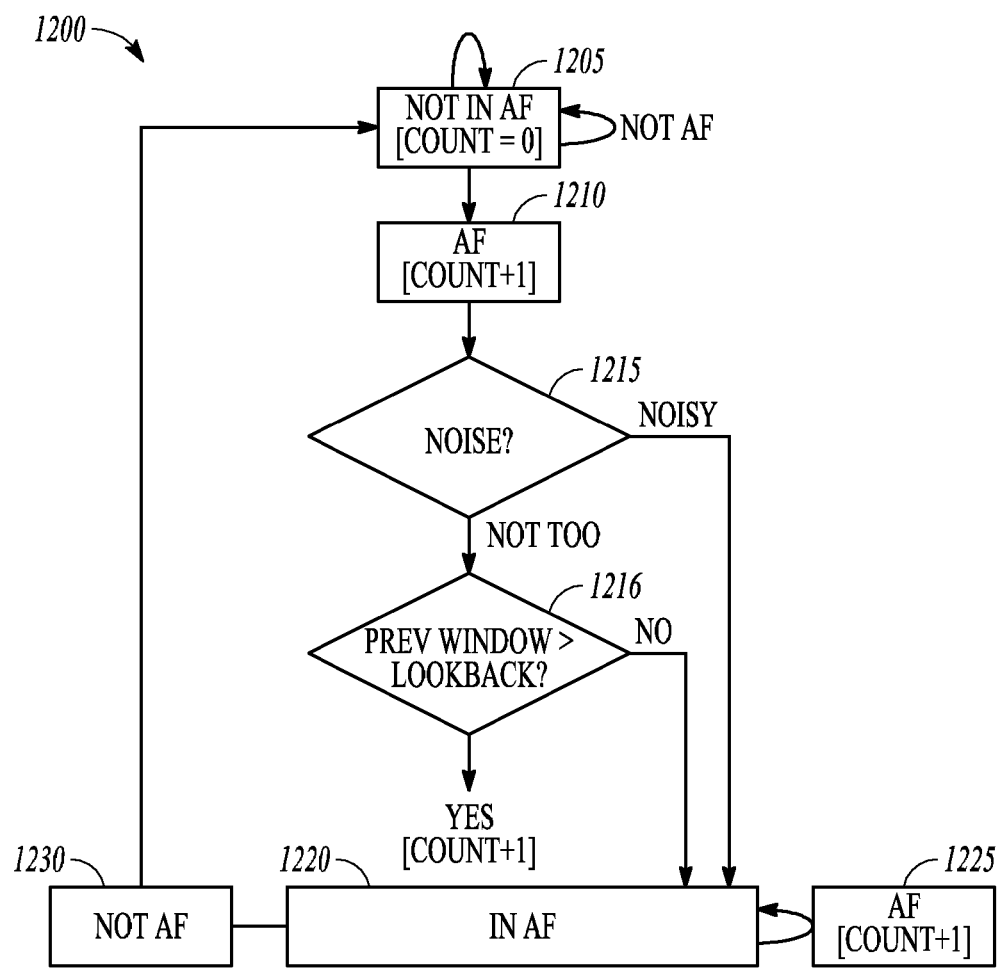
FIG. 12 is a flow diagram of another example of a method of operating an ambulatory medical device.

FIG. 12 is a flow diagram of an example of a method 1200 of determining the time duration an AF episode by counting the number of windows with AF to determine the duration of the detected AF episode. At 1205, the arrhythmia detection circuit 620 looks for AF using the first AF detection criterion or criteria. When AF is detected in a window at 1210, the arrhythmia detection circuit 620 increments the count of detection windows of AF. At 1215, the arrhythmia detection circuit 620 checks the noise of the current window. If the AF detection window is not too noisy, the different look-back AF detection criteria is applied to a previous detection window at 1215.

If AF is detected in the previous non-AF window using the different AF detection criteria, the AF window count is incremented to include the non-AF window, and the process continues applying the first AF detection criteria to new windows at 1220. If the AF window is noisy, the process continues at 1220 and the first AF detection criteria continues to be applied to new windows. If AF continues to be detected, the AF window count is incremented at 1225. If AF is no longer detected, the process returns to looking for AF at 1205. The AF window count can be used to determine the duration of the AF episode. Multiple detected AF episodes can be accumulated into a total time of AF burden for the subject. Returning to FIG. 6, if the total time of AF burden exceeds a threshold, the control circuit 615 of may generate an alert. In certain variations, the alert is a signal transmitted by the medical device. In certain variations, the alert is a flag stored in memory. The alert may be presented using a separate device that communicates with the ambulatory medical device 600. In certain variations, changes can be made to a device-based therapy without generating an alert.

The memory 625 may include an event storage buffer 645. When the episode of AF is detected using the first AF detection criteria, the control circuit 615 triggers storage of sampled values (e.g., an electrogram) of the segment of the sensed cardiac signal that includes the detected episode of AF. This stored cardiac signal can then be later uploaded from the medical device for analysis by a clinician. The control circuit 615 may include a temporary buffer or onset buffer 640 in memory 625 that stores the sensed cardiac signal segment for one or more detection windows. The arrhythmia detection circuit 620 applies the different look-back AF detection criteria to the stored non-AF window when AF is detected in the subsequent detection window. If AF is not detected, the buffer can be over written. When AF is detected in the signal segment stored in the buffer, the stored signal segment can be transferred to the event storage buffer. In variations, the memory portion storing the cardiac signal segment is re-designated as non-temporary storage and the contents are not transferred. The event storage buffer then includes both the detected episode of AF and the sensed cardiac signal prior to the detected episode of AF. In this way, the stored cardiac signal includes the AF onset or start of the AF episode, which may otherwise be lost. Because the actual AF onset may occur during the look back window, the look-back feature can improve accuracy in reporting of the time of the onset of AF. The arrhythmia detection circuit may generate an indication of the start time of the episode of arrhythmia when the episode of arrhythmia is detected in the prior sensed cardiac signal. The indication may be the time of the onset stored in a memory location that can be later uploaded, or the indication of the start time can be included in a report that lists different parameters of the AF episode such as start time and the duration of the episode.

The ambulatory medical device 600 may be a diagnostic-only device, or it may be a device that provides a therapy to the subject. The device may include a therapy circuit 650 that can be electrically coupled to electrodes to provide an anti-arrhythmic cardiac therapy to the subject. The control circuit 615 may initiate delivery of an anti-arrhythmic therapy in response to an indication by the arrhythmia detection circuit 620 that AF is detected. In some examples, the therapy circuit 650 provides electrical pacing therapy to the subject. The control circuit 615 may initiate delivery of the electrical pacing therapy according to a first pacing therapy mode, and change the pacing therapy mode according to the value of total time duration of the detected AF episode. In some examples, the therapy circuit provides cardioversion or defibrillation shock therapy to the subject. The control circuit 615 may initiate delivery of the shock therapy when the total time duration of the detected AF episode exceeds a specified time duration threshold.

The look-back feature of arrhythmia detection can provide post-hoc detection of an arrhythmia. This can provide a more accurate assessment of the arrhythmia detection which can provide device-based analysis of physiologic information that may normally be missed or ignored or provide the additional information to a clinician for analysis.

ADDITIONAL DESCRIPTION

The systems, devices, and methods discussed in this document may improve the medical technology of automated cardiac rhythm management (CRM) and detection and prevention of worsening of cardiac function. The heart rate-based arrhythmia detection may also enhance the performance and functionality of an implantable CRM device, in certain examples, increasing the efficacy of existing AF detection (e.g., by detecting the true onset of AF), such that system performance can be improved with little to no additional cost, while reducing manual inspection required for such detection. In other examples, existing system performance can be maintained (e.g., high AF sensitivity and specificity, etc.) using lower cost or less obtrusive systems, apparatus, and methods. For example, because the system or device does not require direct atrial activity sensing for atrial arrhythmias detection, the system complexity and implementation cost may be reduced. It may particularly be beneficial for patient not indicated for atrial lead implantation either for atrial activity sensing or for atrial pacing. The device-based arrhythmia detection also allows for more efficient use of device memory, such as by correctly storing heart rate statistics that are clinically relevant to arrhythmia recognition. Because onset of AF is more accurately reported, fewer unnecessary drugs and procedures can be scheduled, prescribed, or provided, and the overall management of the patient's cardiac disease can be improved.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:
1. An apparatus comprising:
  a sensing circuit coupled to the arrhythmia detection circuit, and configured to generate a sensed cardiac signal;

an arrhythmia detection circuit configured to:
   detect a cardiac arrhythmia in a first portion of the cardiac signal using a first arrhythmia detection criteria, wherein the cardiac signal is representative of cardiac activity of a subject;
   upon detection of the cardiac arrhythmia, analyze a second portion of the cardiac signal that is prior in time to the first portion using a second different arrhythmia detection criteria to detect the presence or absence of the cardiac arrhythmia in the second portion of the cardiac signal;
   add a duration of the prior sensed cardiac signal to a time duration of an arrhythmia episode when arrhythmia is detected in the prior sensed cardiac signal using the different second detection criteria; and generate a value of total time duration of the arrhythmia episode.

2. The apparatus of claim 1, wherein the arrhythmia detection circuit is configured to: detect an episode of atrial fibrillation (AF) in the sensed cardiac signal using one or more first AF detection criteria and begin timing a duration of the AF episode; apply different AF detection criteria to a duration of the sensed cardiac signal prior to the detected episode of AF when the episode of AF is detected; add the duration of the prior sensed cardiac signal to the time duration of the AF episode when AF is detected in the prior sensed cardiac signal using the different AF detection criteria; and generate a value of total time duration of the detected AF episode.

3. The apparatus of claim 2, wherein the arrhythmia detection circuit is configured to detect the episode of AF from the sensed cardiac signal using a plurality of AF detection criteria having first specificity and first sensitivity to AF detection, and apply a subset of the first AF detection criteria to a segment of the cardiac signal sensed prior to the detected episode of AF with at least one of different specificity or different sensitivity than the first AF detection criterion.

4. The apparatus of claim 2, wherein the arrhythmia detection circuit is configured to detect the episode of AF when sensed ventricular depolarization intervals (V-V intervals) satisfy one or more of a specified V-V interval dispersion threshold, a specified V-V interval double decrement threshold, and a specified Wenkebach AF detection threshold, and classify a segment of the cardiac signal sensed prior to the detected episode as AF when using a change in one or more of the specified V-V interval dispersion threshold, the specified V-V interval double decrement threshold, and the specified Wenkebach AF detection threshold.

5. The apparatus of claim 4, wherein the arrhythmia detection circuit is configured to detect the episode of AF when noise in the sensed cardiac signal is less than a specified noise detection threshold, and classify the segment of the cardiac signal sensed prior to the detected episode as AF when noise in the segment satisfies a different noise detection threshold.

6. The apparatus of claim 2, wherein the arrhythmia detection circuit is configured to apply the first AF detection to the sensed cardiac signal according to sensing windows and count a number of the sensing windows in which AF is detected as the time duration of the AF episode, and add a sensing window prior to a first sensing window in which AF is detected to the count of the number of sensing windows when AF is detected in the prior sensing window using the different AF detection criteria.

7. The apparatus of claim 2, including a control circuit configured to trigger storage of sampled values of a segment of the sensed cardiac signal that includes the detected episode of AF when the episode of AF is detected using the first AF detection criteria, and trigger storage of sampled values of a segment of the cardiac signal that includes both the detected episode of AF and the sensed cardiac signal prior to the detected episode of AF when AF is detected in the prior sensed cardiac signal.

8. The apparatus of claim 2, wherein the arrhythmia detection circuit is configured to accumulate a plurality of detected episodes of AF into a total time of AF burden for the subject and generate an alert according to the total time of AF burden.

9. The apparatus of claim 2, including: a therapy circuit configured to provide electrical pacing therapy to the subject; and a control circuit configured to initiate delivery of the electrical pacing therapy according to a first pacing therapy mode, and change the pacing therapy mode according to the value of total time duration of the detected AF episode.

10. The apparatus of claim 2, including: a therapy circuit configured to provide defibrillation shock therapy to the subject; and a control circuit configured to initiate delivery of the defibrillation shock therapy when the total time duration of the detected AF episode exceeds a specified time duration threshold.

11. The apparatus of claim 1, wherein the arrhythmia detection circuit is configured to generate an indication of the start time of the episode of arrhythmia when the episode of arrhythmia is detected in the prior sensed cardiac signal.

12. A method of controlling operation of an ambulatory medical device, the method comprising:
   sensing a cardiac signal representative of cardiac activity of a subject;
   detecting an episode of cardiac arrhythmia in the sensed cardiac signal using one or more first arrhythmia detection criteria and timing a duration of the arrhythmia episode;
   applying, when the episode of arrhythmia is detected, different one or more arrhythmia detection criteria to a duration of the sensed cardiac signal prior to the detected episode of arrhythmia;
   adding the duration of the prior sensed cardiac signal to the time duration of the arrhythmia episode when arrhythmia is detected in the prior sensed cardiac signal using the different arrhythmia detection criteria; and
   providing a total time duration of the detected arrhythmia episode to a user or process.

13. The method of claim 12, wherein the detecting an episode of arrhythmia includes detecting an episode of atrial fibrillation (AF) in the sensed cardiac signal using one or more first AF detection criteria and timing a duration of the AF episode, wherein the applying the different arrhythmia detection criteria includes applying different one or more AF detection criteria to a duration of the sensed cardiac signal prior to the detected episode of AF when the episode of AF is detected.

14. The method of claim 13, wherein the one or more first AF detection criteria includes a plurality of AF detection criteria having first specificity and first sensitivity to detection of AF, and wherein the different one or more AF detection criteria includes a subset of the first AF detection criteria with at least one of different specificity or different sensitivity than the first AF detection criterion.

15. The method of claim 13, wherein the one or more first AF detection criteria includes detecting when sensed ventricular depolarization intervals (V-V intervals) satisfy one or more of a specified V-V interval dispersion threshold, a specified V-V interval double decrement threshold, and a specified Wenkebach AF detection threshold, and wherein the different one or more AF detection criteria includes a change in one or more of the specified V-V interval dispersion threshold, the specified V-V interval double decrement threshold, and the specified Wenkebach AF detection threshold.

16. The method of claim 15, wherein the one or more first AF detection criteria includes detecting when noise in the sensed cardiac signal is less than a specified noise detection threshold, and wherein the different one or more AF detection criteria includes detecting when noise in the sensed cardia signal is less than a different specified noise detection threshold.

17. The method of claim 13, wherein the detecting the episode of AF includes detecting the episode of AF during a first sensing window, wherein the timing the duration of the AF window includes counting a number of sensing windows with the AF episode, and wherein the adding the duration of the prior sensed cardiac signal to the AF episode includes adding a sensing window prior to the first sensing window to the count of the number of sensing windows with the AF episode.

18. A system comprising:
 a cardiac signal sensing circuit operatively coupled to electrodes and configured to provide a sensed ventricular cardiac signal of a subject; and
 an arrhythmia detection circuit operatively coupled to the cardiac signal sensing circuit and configured to:
  detect an episode of atrial arrhythmia in the sensed ventricular cardiac signal using a first AF detection criteria;
  apply different AF detection criteria to a duration of the sensed cardiac signal prior to the detected episode of atrial arrhythmia upon detection of the episode of atrial arrhythmia; and
  determine a value of total time duration of the detected atrial arrhythmia using a first duration of atrial arrhythmia detected using the first detection criteria and a second duration of atrial arrhythmia using the second detection criteria.

19. The system of claim 18, wherein the arrhythmia detection circuit is configured to detect an episode of AF using a plurality of AF detection criteria to the sensed cardiac signal having first specificity and first sensitivity to AF detection, and apply a subset of the first AF detection criteria to a segment of the cardiac signal sensed prior to the detected episode of AF with at least one of different specificity or different sensitivity than the first AF detection criterion.

* * * * *